United States Patent [19]

Buoncristiani

[11] Patent Number: 4,498,900
[45] Date of Patent: Feb. 12, 1985

[54] METHOD FOR THE AUTOMATIC SEMICONTINUOUS PERITONEAL DIALYSIS

[76] Inventor: Vincenzo Buoncristiani, Via Marco Polo, 4, Foligno, Italy

[21] Appl. No.: 452,513

[22] Filed: Dec. 21, 1982

Related U.S. Application Data

[62] Division of Ser. No. 200,425, Oct. 24, 1980, Pat. No. 4,381,003.

[30] Foreign Application Priority Data

Oct. 26, 1979 [IT] Italy ................................ 43514 A/79

[51] Int. Cl.³ .............................................. A61M 5/00
[52] U.S. Cl. ...................................................... 604/28
[58] Field of Search .............. 604/28, 29; 128/DIG. 3

[56] References Cited

U.S. PATENT DOCUMENTS 3,520,298  7/1970  Lange ..................................... 604/29
3,545,438 12/1970  De Vries ........................... 604/29 X
3,707,967  1/1973  Kitrilakis et al. ...................... 604/29
4,190,047  2/1980  Jacobsen et al. ....................... 604/29

Primary Examiner—Dalton L. Truluck
Attorney, Agent, or Firm—Murray, Whisenhunt and Ferguson

[57] ABSTRACT

A method for the automatic semicontinuous peritoneal dialysis, wherein the dialysing solution is pumped from the supply bag to the peritoneal cavity of the patient in a predetermined amount sensed by control means, by which the pumping means are actuated to change over the pumping direction, the same dialysing solution being pumped to and from the peritoneal cavity for a predetermined number of times.

Patient safety is assured by providing shunting means for the pumping means, whereby the latter are short-circuited between the delivery and the suction side if any abnormal condition occurs.

8 Claims, 3 Drawing Figures

METHOD FOR THE AUTOMATIC SEMICONTINUOUS PERITONEAL DIALYSIS

This is a divisional application of Ser. No. 200,425, filed Oct. 24, 1980, now U.S. Pat. No. 4,381,003.

The present invention relates to a method and apparatus for the automatic semicontinuous peritoneal dialysis.

The peritoneal dialysis consists in the exchange of chemical compounds, through the peritoneal membrane, between the blood, circulating in the blood vessels into contact with the said membrane, and a solution having a suitable composition, which, by means of a proper catheter, is introduced in the peritoneal cavity and removed, when the exchange of the desired chemical compounds has taken place.

To date, the peritoneal dialysis has been carried out in a manually and intermittent manner, according to which the dialysis solution is supplied to and removed from the peritoneal cavity thanks to the force of gravity. It involves several hours of treatment and can be effected either three times a week, with an amount of dialysis solution of about 40 liters and for a time of 10 hours, or daily, with an amount of 10 liters of dialysis liquid and for a time of 2 hours and half.

This method involves not negligible drawbacks and problems, namely:

(a) The patient is compelled to dedicate a great part of time to the dialysis treatment, taking this time away from his social and working life.

(b) The patient is definitely bound to the hospital or clinical center, at which the dialysis treatment is carried out and this dependency is also highly objectionable from the psychological point of view.

(c) There is a high risk of peritoneal infections, because in each treatment bottles of about 2 liters of dialysis solution are used and consequently the number of potentially contaminating acts is high (connection and detachment of the supply bottle from the catheter).

(d) The yield and effectiveness of the treatment as regards the metabolic depuration are often insufficient with respect to the requirements of the patients. Moreover, apart from the true toxic substances, the patient's blood becomes progressively impoverished of non toxic and useful components of the blood. There have been proposed and used in the past semiautomatic or fully automatic equipments, which are able to eliminate or alleviate some of the above mentioned problems and drawbacks.

The advantages of these apparatus can be shortly resumed as follows:

there is no need of a continuous attendance of the patient by the hospital personnel;

there are permitted higher charging and discharging flow rates of the dialysis solution, and thus higher clearances and dialisances, whereby in the time unit a greater amount of toxic substances can be removed from the blood;

there is a greater safety, since most of these apparatus involve sealed circuits, and the tank containing the dialysis solution is connected at once with the inlet catheter, and pumping means periodically operate to introduce fresh solution in the peritoneal cavity, the exhausted solution being thereafter discharged to waste.

However some of the above stated problems and drawbacks remain unchanged and some others added thereto.

In fact the amount of liquid used for each treatment is always high, since the solution is discharged to waste after few minutes of permanence within the peritoneal cavity.

The yield remains also some times unsatisfactory and, due to the use of accelerating pumps (in order to get high flow rates), there is a risk for the well being and some times for the life of the patient (exceedingly high charges, with a very high increase of the interabdominal pressure causing the attendant breathing problems or vagal reflexes with cardiac failure or bloks) and for the operation of the equipment (obstruction of the catheter as caused by parts of the omentum or of the intestinal wall being sucked by the suction force of the discharge pump).

Due to the latter drawbacks these automatic equipments, as a matter of fact, must be used in the day time and with the patient awake, or under the constant survey of an attendant.

There has been recently proposed the ambulatorial continuous peritoneal dialysis (CAPD), consisting in an exchange with 2 liters of dialysis solution every 6 hours; the dialysis liquid remains in the abdomen until the next charge of 2 liters is fed, whereby there is a very long time for the equilibrium to be achieved, thus adding to the yield and the efficacy of the treatment and with the use of a reduced amount of dialysis solution (56 to 70 liters per week). Unfortunately, this system too is affected by a number of problems and drawbacks, namely:

(1) The catheter, for the charging and discharging of the dialysing solution, must be daily opened and closed a high number of times (at least 4 or 5 per day), although the bag containing the solution is worn by the patient even after the transfer to the abdomen of the patient, to reduce the number of connecting and detaching operations.

(2) The constant presence of 2 liters of dialysing solution in the peritoneal cavity causes troubles induced by obstruction and increased pressure (e.g. herniae, hemorrhoids, lumbar pain).

(3) Lastly, a number of patients does not accept to be engaged four times each day, for a time of 45 minutes, with relevant interference with the normal life and the work activity.

The main purpose of the present invention is that of providing a method and apparatus for the peritoneal dialysis in which the problems and drawbacks of the peritoneal dialysis, as carried out up to date, are eliminated in advantageous manner.

Another purpose of the present invention is that of providing a method and an apparatus for the peritoneal dialysis, in which the dialysis treatment does not necessarily have to be carried out in a hospital or dialysis center, can be effected without the attendance of specialized personnel and can be effected in the nightime, when the patient is asleep, the apparatus comprising safety means by which whatever risk of damage to the patient is avoided.

A further purpose of the present invention is that of providing a method and an apparatus for the peritoneal dialysis, in which the risk of infections due to the manual operations is essentially eliminated, and the dialysis attains the required satisfactory levels of yield and efficacy.

These and other purposes are achieved with a method and apparatus for the peritoneal dialysis, wherein a dialysing solution is, introduced in the peritoneal cavity of the patient, characterized in that the dialysing solution in an amount consistent with the single patient undergoing the treatment, is fed by pumping means to the peritoneal cavity of the patient, possibly maintained therein for a predetermined time, and then pumped back from the said cavity to a tank of dialysing solution in a closed circulation system, the temperature of the dialysing solution in said tank being controlled at a desired value, and said pumping means comprising safety means including both control means sensing the amount of dialysing solution pumped in the peritoneal cavity and adapted to stop the operation of said pumping means and safety means by which the delivery and suction sides of the pumping means are connected to each other in the case of increase of the pressure, either in the charging and/or in the discharging phases.

The features and advantages of the present invention shall appear from the following detailed description of a preferred embodiment of the apparatus of the invention, with reference to the enclosed drawings in which.

Figure 1:
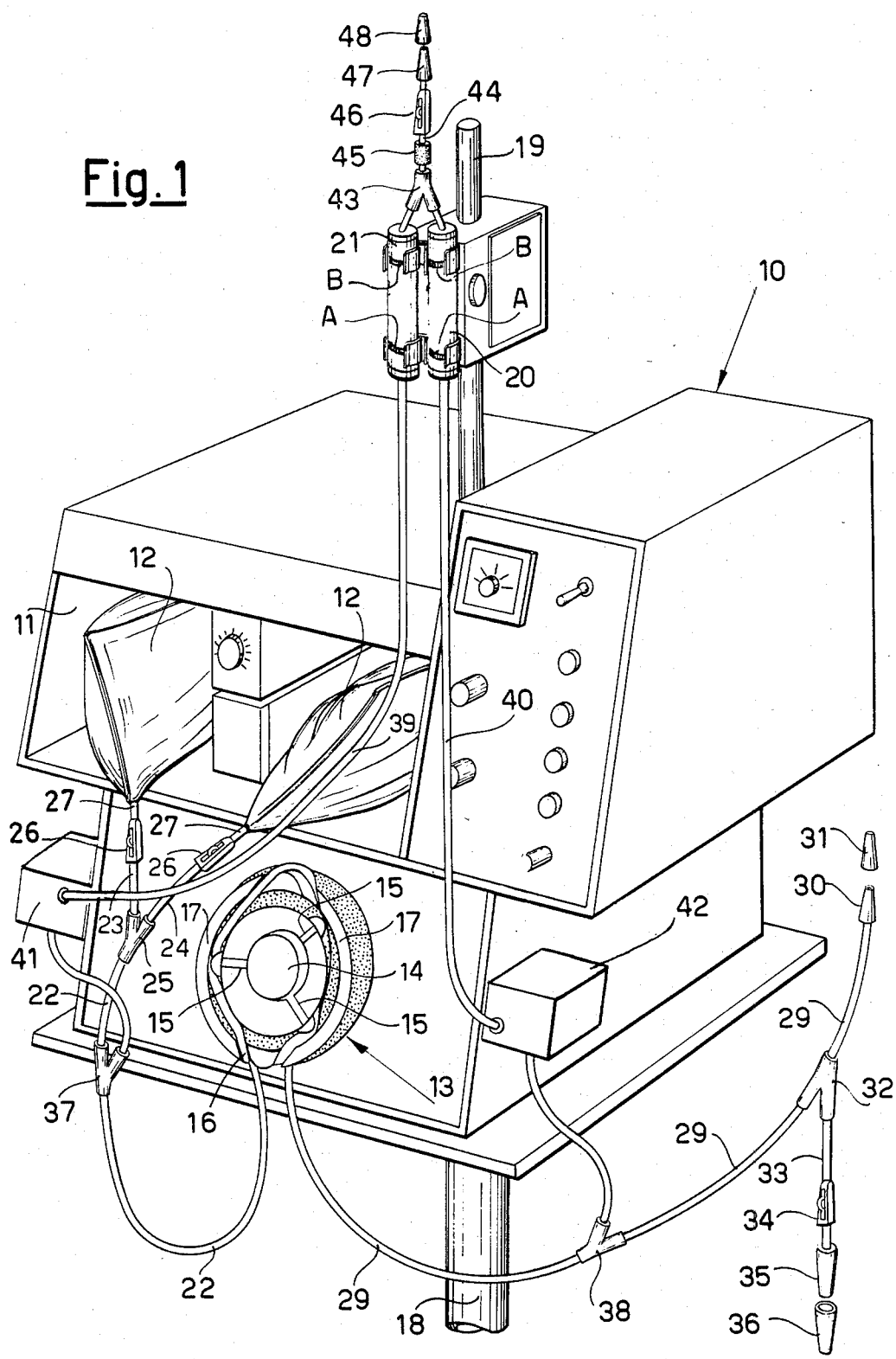
FIG. 1 is a general isometric view of the apparatus of the invention.

Referring to FIG. 1 the apparatus of the invention comprises a casing 10, in which a chamber 11 is provided, having an automatic radiating heating system and thermostatic means (not shown) for the temperature control. In the chamber 11 at least one soft bag 12 is provided, containing a supply of a solution suitable for the dialysis. The chamber 11 and/or the flow set are provided with sterilizing means (e.g. ultraviolet lamps), by which the environment containing the dialysing solution and the detachable connections to the flow set is maintained in a sterile status.

In the front part of the housing 10, a peristaltic pump 13 is mounted, the pump 13 being of the type comprising a rotating hub 14, bearing roller arms 15 adapted to engage the outer surface of a flexible pipe 16 and press it against a cicular wall 17, whereby the pipe throttled between the roller tip of the arms 15 and the wall 17 and the liquid contained within the pipe 16 is pumped in the direction of rotation of the hub 14.

These peristaltic pumps are well known in the art. whereby no further disclosure is necessary, it being enough to indicate that the hub 14 is driven by a suitable electric motor (not shown) and rotates in both directions.

The casing 10 is supported by an adjustable leg 18, whereas to the stand 19, protruding from the upper surface of the casing 10, there are adjustably mounted two level detecting cells 20 and 21, in which two levels A and B are detected for the purposes hereinafter described.

The afore said cells are electrically connected to the electrical circuit comprising the timing means by which the operation of the pump is controlled.

Figure 2:
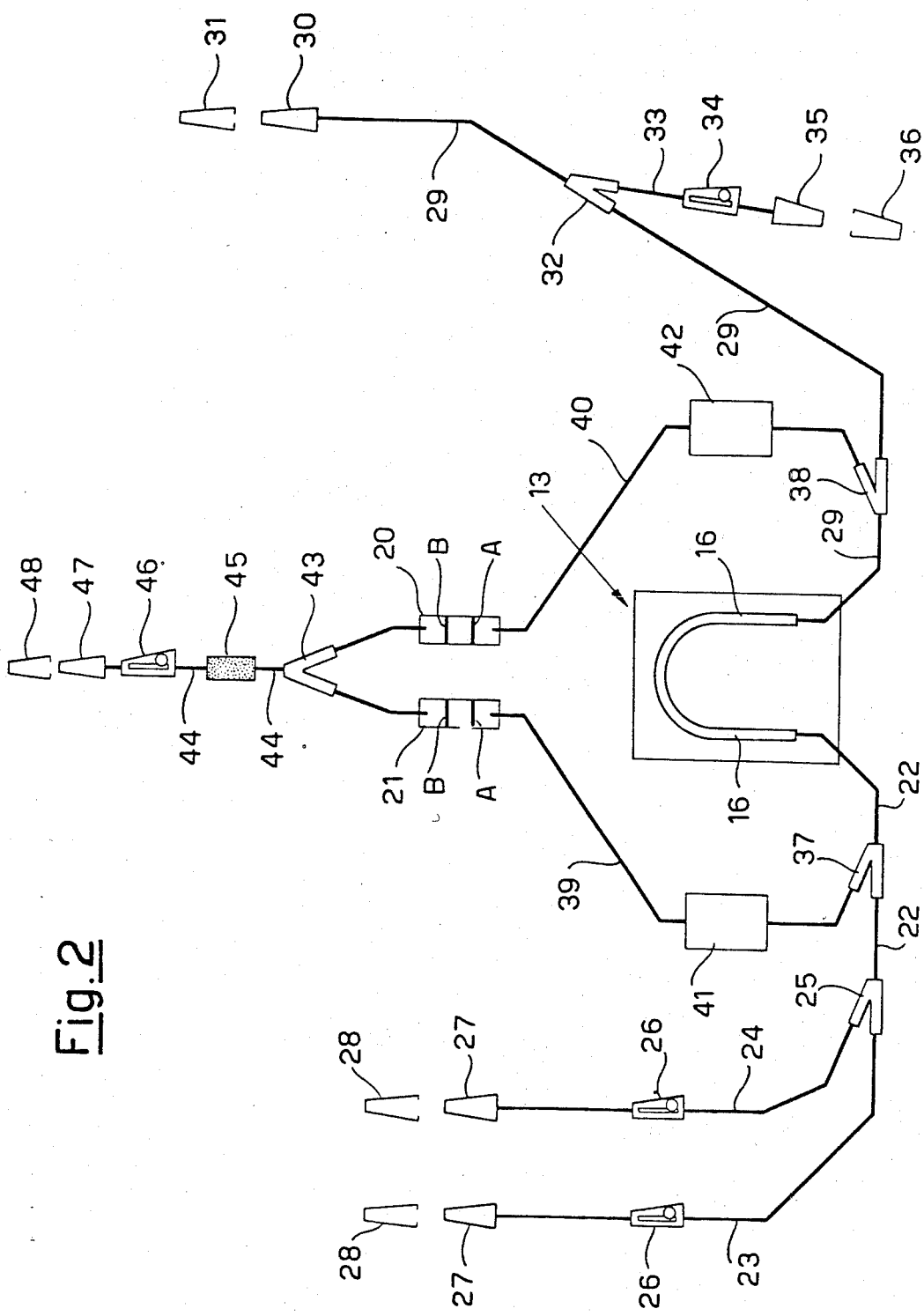
FIG. 2 is a schematic view of the flow set for the dialysing solution.

Turning now to the FIG. 2, which shows the disposable flow set of the apparatus, the peristaltic pump is represented by the block 13, in which the flexible pipe 16 passes. The pump 13 is connected by the suction flexible pipe 22 to the supply bags 12 (not shown in FIG. 2) through the branches 23 and 24 (connected to the pipe 22 by a two way fitting 25), the manually operable throttling valve 26, and the inlet fittings 27, the latter being designed for a quick connection to the inlet of the related bag. Plugs 28 serve to keep the fittings 27 closed in an completely seal tight manner, until the connection to the bag is made.

The delivery flexible pipe 29 connects the pump 13 to the patient through a fitting 30, adapted for a quick connection to the catheter (not shown) permanently implanted in the patient abdomen for the connection of the pump to the peritoneal cavity thereof.

A plug 31 has the same function as the plugs 29 of the suction side. Of course in the discharge phase the pipe 29 becomes the suction side and the pipe 22 becomes the delivery side of the pump 13.

A branching fitting 32, together with the pipe 33, the manually operable throttling valve 34, the fitting 35 and the plug 36, serves as a safety pressure release device, in case of overpressure in the pipe 29.

Upstream and downstream of the pump 13 two shunting fittings 37 and 38 are provided, leading to the shunt ducts 39 and 40, in which respective compensation tanks 41 and 42 are provided (for the hereinafter stated purpose) the cells 20 and 21 being serially connected to the said shunt ducts, 40 and 39 respectively. Downstream of the cells 20 and 21, the ducts 39 and 40 merge, through a fitting 43, into only one duct 44, comprising a sterile filter 45, a manually operable throttling valve 46 and a fitting 47, closed by a plug 48.

Figure 3:
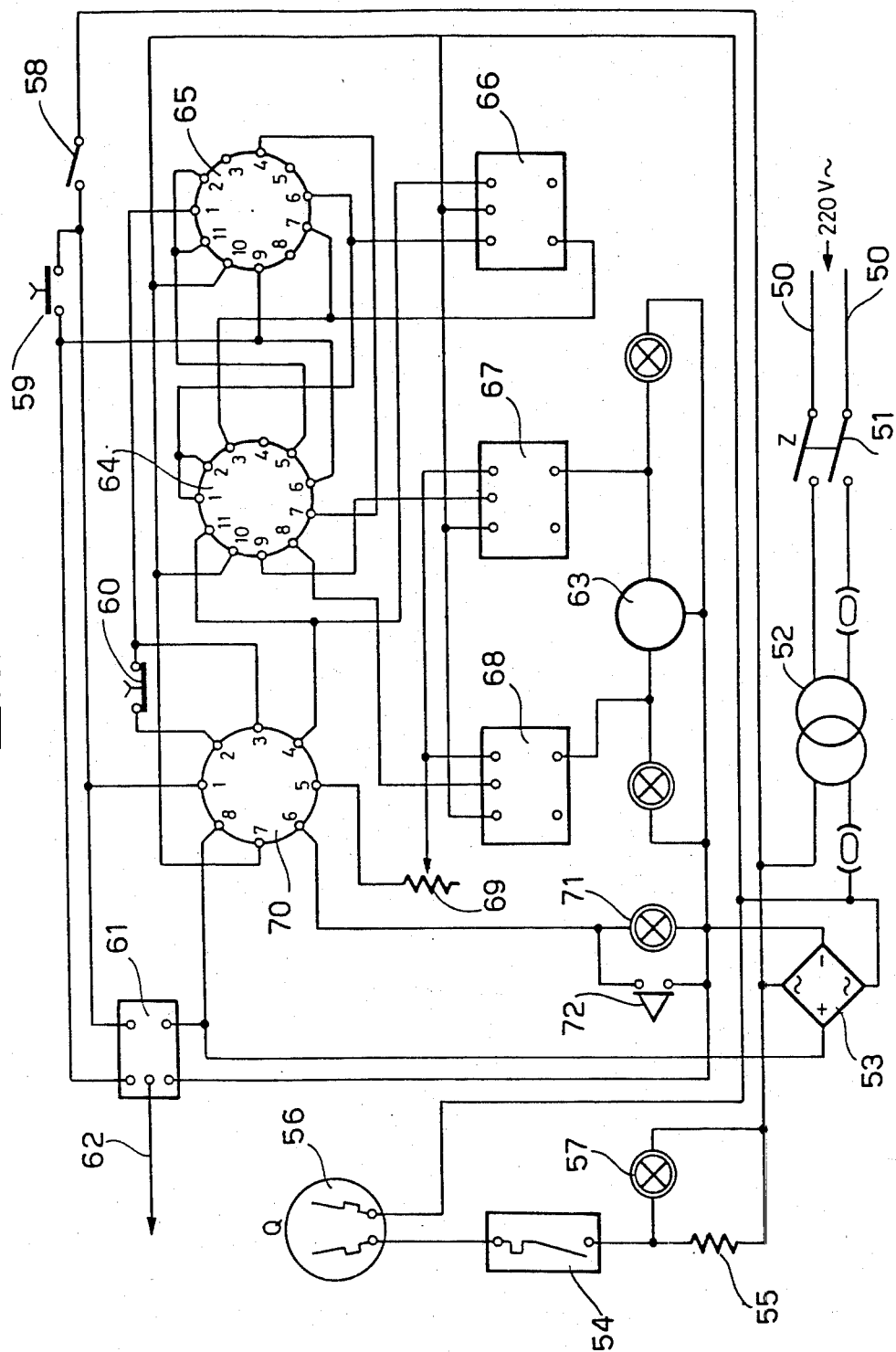
FIG. 3 is a schematic view of the electric circuit of the apparatus.

Turning now to the electrical circuit shown in FIG. 3 (which has only illustrative purpose of one embodiment of the apparatus), the electrical power from the mains 50, through the main switch 51, the transformer 52 and the rectifying bridge 53, is fed to the apparatus at a voltage of 24 or 12 volts maximum, for sake of safety.

The adjusting thermostat 54, as controlled by the variable resistor 55, is serially connected to the maximum thermostat 56, in turn connected to the warning lamp 57, and permits the temperature of the chamber 11 and thus of the dialysing solution to be carefully controlled to the desired value and to be prevented from becoming exceedingly high, the thermostat 56 being not accessible from outside of the apparatus.

The button 58 permits the operation of the apparatus to be started, whereas push buttons 59 and 60 are auxiliary switches to be actuated in case of abnormal operation of the apparatus.

The level detecting cells 20 and 21 are electrically connected to the control circuit by the connecting device 61, through the conductor 62 (corresponding to the sensing level B, whereas at the level A the related conductor of the cells is grounded). The operation of the pump, the motor of which is represented by 63, is controlled by the relays 64 and 65 and the timer 66, whilst the time delaying devices 67 and 68 ensure that a time delay is left before the motor 63 of the pump starts the rotation in the opposite direction with respect to the next preceding phase. The rotation speed of the motor 63 is controlled and adjusted by means of the potentiometer 69, whereas the relay 70, responsive to an abnormal condition as signalled by the cells 20 and 21, causes the motor 63 to be stopped and the warning light 71, as well as the warning bell 72, to be switched on.

Considering now the method of the invention, as embodied by the apparatus, it is to be pointed out that the main feature of this method resides in that the same dialysing solution is circulated in a closed circuit between the supply bag 12 and the peritoneal cavity of the patient. In fact it has been surprisingly found that by continuously circulating the dialysing solution from the bag 12 to the peritoneal cavity and back to the bag, the amounts of the several uremic toxic substances (urea, creatinine, uric acid, phosphorous, etc.) as daily removed from the blood are the same as those removed by the prior art systems.

In the preferred embodiment of the method of the invention, the amount of dialysing solution as contained in the supply bag (or bags) 12, is greater than the amount really fed, per each cycle, to the patient's peritoneal cavity, whereby the volume of dialysing solution pumped back from the peritoneal cavity to the supply bag is admixed with the solution already present in the bag and then another volume of the same solution is pumped again within the peritoneal cavity for the next exchange phase.

Although no definite explanation of the results obtained with the method of the invention has been given to date, it seems feasible that these results are attained thanks:

(1) to the extended contact time of the same solution with the peritoneal membrane within the peritoneal cavity;

(2) to the continuous admixing and recycling of the dialysing solution;

(3) to the higher turbulence of the solution present in the peritoneal cavity as resulting from the continuous recycling. In fact, in the preferred embodiment of the method of the invention, the dialysing solution is pumped into the peritoneal cavity and then pumped back to the supply bag and so on, the said phases being automatically controlled to take place in the desired sequence and either the one immediately after the other or with a predetermined short time delay between the charging and the discharging phases.

Another advantage of the method of the invention resides in that the operation is carried out in a wholly closed circuit, the connecting operations being carried only at the very beginning and at the end of the treatment, with a highly reduced danger of sepsis. Turning now to the operation of the apparatus of the invention, it is to be pointed out that all the pipe connections, the fittings, the supply bags, etc. (apart from the pump, the casing 10 and the other components, which do not come into contact with the dialysing solution) are disposable and of a suitable plastic material, whereby each treatment is carried out with a fully reliable flow set, the several plugs being removed only at the time of the connection to the supply bags and to the permanent catheter of the patient.

Another feature to be pointed out is that the supply bags 12, the pump 13, the compensating tanks 41, 42 and the patients abdomen should be as much as possible at the same level, to avoid unnecessary variations of the pressure and of the flow resistance on either side of the pump.

When the thermostatic control means 54, 55, 56, cause the temperature of the cavity 11 to attain the desired value (as signalled by the switching off of the lamp 57) operation of the apparatus is initiated by closing switch 58 and the the pump 13 starts the feeding of dialysing solution from the bag (bags) 12 to the peritoneal cavity of the patient.

In this connection it is to be pointed out that the exact volume of dialysing solution pumped in the charging phase varies from a patient to another and can be readily adjusted, for instance by adjusting the flow rate delivered by the pump.

The pump operation shall give place in the delivery pipe 29 to a certain pressure and the same pressure will occur in the branch duct 40, whereby the solution will raise in this duct simultaneously to the feeding of solution to the peritoneal cavity, attaining the level B in the sensing cell 20.

Once the peritoneal cavity is filled with the desired amount of dialysing solution, the resistance opposed to the liquid flow in the pipe 29 will increase, whereby the liquid level in the branch duct 40 will increase until the level A in the cell 20 is attained. At this point the signal originated from the cell 20 causes the motor 63 to stop and then, after the predetermined delay to invert the direction of rotation. Consequently the discharge of the dialysing solution from the peritoneal cavity will start, it being pumped back to bag or bags 12.

The same operation sequence, as above stated for the branch duct 40 and the cell 20, does occur now for the branch duct 39 and in the cell 21, until the level A is attained in the latter, whereby the charging phase is started again.

In the case in which an abnormal condition occurs, such as for instance the obstruction of the catheter in the discharging phase due to the suction acting in the peritoneal cavity, the pressure does immediately increase in the branch duct and the liquid level attains the level A; however the relay 70 and the timer 66 are not yet in the configuration they must have at the end of the discharge phase whereby the warning lamp 71 and the warning bell 72 are actuated and the patient is able to manually intervene by operating the push button 60. In this way the cycle is immediately changed over from the discharging phase to the charging phase and the reverse action tending to eliminate the catheter obstruction takes place. The duration of this attempt (which is normally sufficient) is controlled by means of the push button 59. In the case of failure of the cells 20 and 21 or of any other component of the controlling circuit, both in the charging and in the discharging phase, whereby no change over signal is transmitted to the motor 63, the liquid level in either the cell 20 or in the cell 21 will be further increased by a very short distance until the fitting 43 is attained and then the liquid will pass through the other cell, whereby the further pressure as generated by the pump will be discharged to the suction side, without danger and damage for the patient. In the latter case, in order to restore the apparatus, it is enough to remove the plug 48, thus causing both branch ducts 39 and 40 to become free of liquid by gravity, and then restart the operation by closing again the fitting 47, the filter 45 preventing any contamination of the flow set.

In order to compensate the possible different lengths of the pipes connecting the pump 13 both with the supply bag (bags) 12 and with the patient, as well as to compensate possible differences in the flow resistances shown by the several pipes and ducts both in the charging and in the discharging phase, the compensating tanks 41 and 42 are adjustable as to their height with respect to the level position, provided that when the one is raised the other is lowered by the same distance and viceversa. In the figures the mounting and adjusting means are not shown, it being in the reach of the man skilled in the art.

From the preceding disclosure it will be understood that the method and apparatus of the present invention permit the peritoneal dialysis to be effected automatically and in a time of choice for the patient, preferably in the night time and with the patient asleep. In fact, there is no risk for the patient, since even a failure of the cells 20 and 21 controlling the operation of the pump does just involve the short circuiting of the pump.

Consequently the same advantages of the C.A.P.D. system are achieved (as regards the efficacy of the dialysis treatment and the reduced amount of dialysis solution employed for each treatment, normally 10 liters), but without the stated drawbacks for the patient. Furthermore, there are possible higher flow rates of the charging and discharging phases, without objectionable consequences for the patient, as it would occur in the prior art apparatus.

The apparatus of the invention has been described with reference to a preferred embodiment, but changes and modifications are possible within the scope of the invention.

I claim:

1. A method for automatic semicontinuous peritoneal dialysis of a patient in need of such dialysis, wherein dialysing solution is introduced into the peritoneal cavity of the patient and then discharged therefrom, comprising forming a closed circuit between said peritoneal cavity and a supply of dialysing solution, said supply of dialysing solution being a predetermined amount of solution; transferring the dialysing solution from said supply, in an amount predetermined consistently with the patient undergoing the treatment, to the peritoneal cavity of the patient in unchanged form from that in said supply; transferring at least a portion of said dialysing solution back from said cavity to said supply in unchanged form from that in which it is withdrawn from said cavity; and sequentially repeating said transfer of the dialysing solution to and from the said peritoneal cavity for a predetermined number of cycles, while maintaining the dialysing solution at a desired temperature.

2. The method according to claim 1, wherein the amount of dialysing solution fed to and pumped back from the peritoneal cavity is detected each time in both phases of every cycle, by means of sensing means for preventing an amount of dialysing solution greater than the said predetermined amount from being pumped into the peritoneal cavity.

3. The method according to claim 2, wherein said prevention of a greater than predetermined amount being pumped to the peritoneal cavity is ensured by short-circuiting the suction and delivery sides of said pumping means, when said sensing means are not actuated upon the said predetermined amount having been pumped into the peritoneal cavity.

4. In a method for conducting automatic semicontinuous peritoneal dialysis, wherein a dialysing solution is introduced into the peritoneal cavity of a patient in need of such dialysis and then discharged from the peritoneal cavity, the improvement comprising the steps of:

(a) providing a supply of dialysing solution, said supply being in an amount predetermined in accordance with the patient undergoing peritoneal dialysis;

(b) providing a pumping means for pumping said dialysing solution to and from said supply of dialysing solution and said peritoneal cavity, said supply, said peritoneal cavity and said pumping means being connected together in a closed circuit;

(c) introducing at least a portion of said dialysing solution from said supply into said peritoneal cavity in unchanged form from that in said supply through said closed circuit by operation of said pumping means;

(d) removing at least a portion of said dialysing solution in said peritoneal cavity from said cavity and transferring all of said removed dialysing solution in unchanged form from that in which it is removed from said cavity to said supply of dialysing solution through said closed circuit by operation of said pumping means;

(e) sequentially repeating steps (c) and (d) for a predetermined number of cycles to repeatedly transfer at least portions of the same dialysing solution initially present in said supply through said closed circuit to and from said peritoneal cavity and said supply of dialysing solution, whereby the risk of peritoneal infection in the patient due to exterior exposure of dialysis solution is essentially eliminated.

5. A method according to claim 4, wherein said predetermined amount of said dialysing solution is greater than the amount of dialysing solution introduced into said peritoneal cavity during each cycle, said portion of said dialysing solution being transferred from said peritoneal cavity to said supply being admixed with dialysing solution already present in said supply to give an admixed dialysing solution, a portion of which is then introduced into said peritoneal cavity in the next succeeding cycle.

6. A method according to claim 4, wherein said predetermined amount of dialysing solution introduced into said peritoneal cavity is detected, and the amount of dialysing solution subsequently introduced into said peritoneal cavity is controlled to prevent an amount of dialysing solution greater than said predetermined amount being introduced into said peritoneal cavity.

7. A method according to claim 6, wherein said amount of dialysing solution subsequently fed to said peritoneal cavity is controlled so as not to exceed said predetermined amount of dialysing solution by passing said dialysing solution through a short circuit connected upstream and downstream of said pumping means.

8. A method according to claim 4, wherein said dialysing solution is maintained at a desired temperature.

* * * * *